(12) United States Patent (10) Patent No.: US 10,251,689 B2
Jacofsky et al. (45) Date of Patent: Apr. 9, 2019

(54) PLACEMENT TOOL FOR BONE SCREW ASSEMBLY, AND SYSTEMS AND METHODS OF USING SAME

(71) Applicant: The Center for Orthopedic Research And Education, Inc., Phoenix, AZ (US)

(72) Inventors: Marc C. Jacofsky, Phoenix, AZ (US); A. Joshua Appel, Hallandale, FL (US)

(73) Assignee: The Center for Orthopedic Research And Education, Inc., Phoenix, AZ (US)

( * ) Notice: Subject to any disclaimer, the term of this patent is extended or adjusted under 35 U.S.C. 154(b) by 0 days.

(21) Appl. No.: 14/790,557

(22) Filed: Jul. 2, 2015

(65) Prior Publication Data

US 2015/0297276 A1    Oct. 22, 2015

Related U.S. Application Data

(62) Division of application No. 12/383,769, filed on Mar. 25, 2009, now Pat. No. 9,072,561.
(Continued)

(51) Int. Cl.
*A61B 17/68* (2006.01)
*A61B 17/86* (2006.01)
(Continued)

(52) U.S. Cl.
CPC ........ *A61B 17/8685* (2013.01); *A61B 17/686* (2013.01); *A61B 17/7064* (2013.01);
(Continued)

(58) Field of Classification Search
CPC . A61B 17/686; A61B 17/8685; A61B 17/863; A61B 17/864; A61B 2017/681
See application file for complete search history.

(56) References Cited

U.S. PATENT DOCUMENTS 2,381,050 A    8/1945 Hardinge
4,013,071 A *  3/1977 Rosenberg ........... A61B 17/686
                                                411/397
(Continued)

OTHER PUBLICATIONS

Restriction Requirement dated Aug. 2, 2011 by the USPTO for U.S. Appl. No. 12/383,769, filed Mar. 25, 2009, and granted as U.S. Pat. No. 9,072,561 on Jul. 7, 2015 (Inventor—Marc C. Jacofsky) (10 pages).

(Continued)

*Primary Examiner* — Samuel S Hanna
(74) *Attorney, Agent, or Firm* — Ballard Spahr LLP (57) ABSTRACT

A placement tool for positioning a multipart cannulated screw assembly to fixate first and second bone elements. The placement tool includes a stem and a head carried on the stem. The head has an outer shank engagement provision that engages the proximal end of an outer shank of a bone screw assembly and permits selective rotation of the outer shank. The head also has an inner shank engagement provision that engages the proximal end of an inner shank of the bone screw assembly and permits selective rotation of the inner shank. The inner shank and outer shank engagement provisions are connectable to one another such that the inner shank and outer shank engagement provisions rotate together.

10 Claims, 10 Drawing Sheets

Related U.S. Application Data (60) Provisional application No. 61/070,795, filed on Mar. 25, 2008.

(51) Int. Cl.
    *A61B 17/70*     (2006.01)
    *A61B 17/88*     (2006.01)
    *A61B 17/56*     (2006.01)

(52) U.S. Cl.
    CPC ........ *A61B 17/864* (2013.01); *A61B 17/8877* (2013.01); *A61B 2017/564* (2013.01)

(56) References Cited

U.S. PATENT DOCUMENTS

| | | | |
|---|---|---|---|
| 5,129,901 | A | 7/1992 | Decoste |
| 5,209,753 | A | 5/1993 | Biedermann et al. |
| 5,470,230 | A | 11/1995 | Daftary et al. |
| 5,702,216 | A | 12/1997 | Wu |
| 5,769,852 | A | 6/1998 | Brånemark |
| 5,827,285 | A | 10/1998 | Bramlet |
| 5,899,906 | A | 5/1999 | Schenk |
| 6,142,782 | A | 11/2000 | Lazarof |
| 6,332,778 | B1 | 12/2001 | Choung |
| 6,458,134 | B1 | 10/2002 | Songer et al. |
| 6,485,518 | B1 | 11/2002 | Cornwall et al. |
| 6,668,688 | B2 * | 12/2003 | Zhao ............... A61B 17/8685 411/51 |
| 6,991,461 | B2 | 1/2006 | Gittleman |
| 7,381,213 | B2 | 6/2008 | Lizardi |
| 8,057,524 | B2 | 11/2011 | Meridew |
| 8,388,660 | B1 | 3/2013 | Abdou |
| 9,072,561 | B2 | 7/2015 | Jacofsky et al. |
| 2002/0049447 | A1 | 4/2002 | Li |
| 2002/0147454 | A1 | 10/2002 | Neto |
| 2003/0032965 | A1 * | 2/2003 | Schneiderman ... A61B 17/1757 606/102 |
| 2003/0187447 | A1 | 10/2003 | Ferrante et al. |
| 2004/0030336 | A1 | 2/2004 | Khanna |
| 2004/0172031 | A1 * | 9/2004 | Rubecamp ......... A61B 17/8685 606/309 |
| 2004/0210227 | A1 | 10/2004 | Trail et al. |
| 2006/0106390 | A1 | 5/2006 | Jensen et al. |
| 2007/0038221 | A1 | 2/2007 | Fine et al. |
| 2008/0045963 | A1 | 2/2008 | Abdou |
| 2008/0065094 | A1 | 3/2008 | Assell et al. |
| 2008/0147127 | A1 | 6/2008 | Tipirneni et al. |
| 2009/0198245 | A1 * | 8/2009 | Phan ................. A61B 17/7065 606/99 |
| 2009/0248089 | A1 | 10/2009 | Jacofsky et al. |

OTHER PUBLICATIONS

Response to Restriction Requirement dated Aug. 30, 2011 to the USPTO for U.S. Appl. No. 12/383,769, filed Mar. 25, 2009, and granted as U.S. Pat. No. 9,072,561 on Jul. 7, 2015 (Inventor—Marc C. Jacofsky) (1 page).

Supplemental Response to Restriction Requirement dated Sep. 27, 2011 to the USPTO for U.S. Appl. No. 12/383,769, filed Mar. 25, 2009, and granted as U.S. Pat. No. 9,072,561 on Jul. 7, 2015 (Inventor—Marc C. Jacofsky) (3 pages).

Non Final Rejection dated Nov. 29, 2011 by the USPTO for U.S. Appl. No. 12/383,769, filed Mar. 25, 2009, and granted as U.S. Pat. No. 9,072,561 on Jul. 7, 2015 (Inventor—Marc C. Jacofsky ) (7 pages).

Response Non Final Rejection dated Mar. 8, 2012 to the USPTO for U.S. Appl. No. 12/383,769, filed Mar. 25, 2009, and granted as U.S. Pat. No. 9,072,561 on Jul. 7, 2015 (Inventor—Marc C. Jacofsky ) (10 pages).

Final Rejection dated Apr. 4, 2012 by the USPTO for U.S. Appl. No. 12/383,769, filed Mar. 25, 2009, and granted as U.S. Pat. No. 9,072,561 on Jul. 7, 2015 (Inventor—Marc C. Jacofsky) (8 pages).

Response Final Rejection dated Jun. 6, 2012 to the USPTO for U.S. Appl. No. 12/383,769, filed Mar. 25, 2009, and granted as U.S. Pat. No. 9,072,561 on Jul. 7, 2015 (Inventor—Marc C. Jacofsky ) (14 pages).

Request for Continued Examination dated Aug. 6, 2012 to the USPTO for U.S. Appl. No. 12/383,769, filed Mar. 25, 2009, and granted as U.S. Pat. No. 9,072,561 on Jul. 7, 2015 (Inventor—Marc C. Jacofsky) (16 pages).

Non Final Rejection dated Dec. 19, 2012 by the USPTO for U.S. Appl. No. 12/383,769, filed Mar. 25, 2009, and granted as U.S. Pat. No. 9,072,561 on Jul. 7, 2015 (Inventor—Marc C. Jacofsky ) (8 pages).

Response Non Final Rejection dated May 16, 2013 to the USPTO for U.S. Appl. No. 12/383,769, filed Mar. 25, 2009, and granted as U.S. Pat. No. 9,072,561 on Jul. 7, 2015 (Inventor—Marc C. Jacofsky ) (12 pages).

Final Rejection dated Jul. 25, 2013 by the USPTO for U.S. Appl. No. 12/383,769, filed Mar. 25, 2009, and granted as U.S. Pat. No. 9,072,561 on Jul. 7, 2015 (Inventor—Marc C. Jacofsky) (12 pages).

Request for Continued Examination dated Oct. 23, 2013 to the USPTO for U.S. Appl. No. 12/383,769, filed Mar. 25, 2009, and granted as U.S. Pat. No. 9,072,561 on Jul. 7, 2015 (Inventor—Marc C. Jacofsky) (16 pages).

Non Final Rejection dated Jun. 26, 2014 by the USPTO for U.S. Appl. No. 12/383,769, filed Mar. 25, 2009, and granted as U.S. Pat. No. 9,072,561 on Jul. 7, 2015 (Inventor—Marc C. Jacofsky) (10 pages).

Response Non Final Rejection dated Oct. 27, 2014 to the USPTO for U.S. Appl. No. 12/383,769, filed Mar. 25, 2009, and granted as U.S. Pat. No. 9,072,561 on Jul. 7, 2015 (Inventor—Marc C. Jacofsky ) (12 pages).

Final Rejection dated Nov. 14, 2014 by the USPTO for U.S. Appl. No. 12/383,769, filed Mar. 25, 2009, and granted as U.S. Pat. No. 9,072,561 on Jul. 7, 2015 (Inventor—Marc C. Jacofsky) (11 pages).

Request for Continued Examination dated Feb. 17, 2015 to the USPTO for U.S. Appl. No. 12/383,769, filed Mar. 25, 2009, and granted as U.S. Pat. No. 9,072,561 on Jul. 7, 2015 (Inventor—Marc C. Jacofsky) (21 pages).

Notice of Allowance dated Mar. 13, 2015 by the USPTO for U.S. Appl. No. 12/383,769, filed Mar. 25, 2009, and granted as U.S. Pat. No. 9,072,561 on Jul. 7, 2015 (Inventor—Marc C. Jacofsky) (7 pages).

Issue Notification dated Jun. 17, 2015 by the USPTO for U.S. Appl. No. 12/383,769, filed Mar. 25, 2009, and granted as U.S. Pat. No. 9,072,561 on Jul. 7, 2015 (Inventor—Marc C. Jacofsky) (1 page).

* cited by examiner

PLACEMENT TOOL FOR BONE SCREW ASSEMBLY, AND SYSTEMS AND METHODS OF USING SAME

CROSS-REFERENCE TO RELATED APPLICATIONS

This application is a divisional of co-pending U.S. patent application Ser. No. 12/383,769, filed Mar. 25, 2009, which claims priority to and the benefit of U.S. Provisional Patent Application No. 61/070,795, filed Mar. 25, 2008, which applications are incorporated herein by reference in their entirety.

FIELD

The present invention relates to a screw for the fixation of the facet joints of the human spine. More particularly, the invention relates to a device that is designed for use in the lower thoracic and lumbar spine, but may have wider application in general orthopedic uses including fracture fixation and implant fixation.

BACKGROUND

Figure 18:
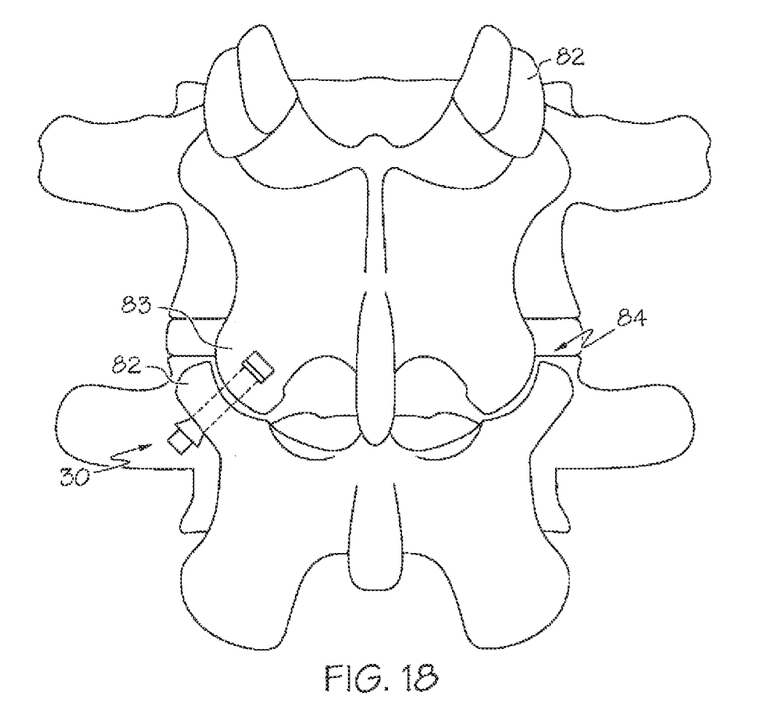
FIG. 18 is a perspective view of a cannulated screw assembly disposed within a facet joint, according to an embodiment of the present invention.

The facet joints, or zygapophyseal joints, of the spine are located at two symmetrical locations at the posterior of the vertebral column. Each facet joint consists of two overlapping bony protrusions, the superior articular process of one vertebrae and the inferior articular process of the neighboring vertebrae. FIG. 18 illustrates two vertebrae as they mate at the facet or zygapophyseal joints.

In certain cases of degeneration of the spinal disk, instability of vertebral segments, arthritis of the facet joint, or trauma, partial or complete immobilization of one or more facet joints is desirable. Traditionally, immobilization is accomplished by anchoring orthopedic hardware into the vertebral bodies of adjacent segments, often through the pedicle, and interposing a plate or rod between the vertebrae to limit motion. Additionally, interbody devices are often placed into the disc space through a variety of techniques to further limit motion and promote bony fusion between adjacent vertebrae. However, for a number of reasons, it would be advantageous to eliminate motion and improve stability between two or more vertebrae by directly fastening one or both of the facet joints together. From a surgical perspective, the facet joint is easily accessible, thus reducing operative time, decreasing blood loss, decreasing incision size, reducing incidence of reoperation, and decreasing the risk of potential deleterious effects on nearby anatomic structures, including spinal nerve roots and the spinal cord itself. Further, fixation at the facet joints is more biomechanically desirable because the center of rotation of the lumbar spine for flexion and extension is located nearest to the facet joints. Thus, placing an immobilization device at or through the facet joint decreases the torque transmitted through the device, which in turn may prevent loosening or premature device failure.

In order to provide effective fixation of the facet joint, a few challenges must be overcome. Most importantly, a fixation device must create compression between the two articular processes. The compression, which causes or enhances immobilization of the joint by encouraging stability throughout the joint, must be maintained for a significant period of time. Additionally, loosening of the device must be prevented. Because the facet joint is generally a mobile joint, forces will continue to be transmitted through the joint after the insertion of an immobilization device. Without a specific way to prevent loosening of the device, loosening will likely occur as the result of micromotion. Once a device has loosened, the device will often begin to protrude from or back-out of the bone, causing significant discomfort, damage to the joint, or danger to surrounding tissues.

Other devices, such as various types of bone screws, have been offered as ways to fasten the facet joints together. However, each previously proposed fixation device has suffered significant shortcomings. For example, a standard fully threaded bone screw may be sufficient for merely adjoining two surfaces. However, a fully threaded screw is not capable of creating any significant amount of compression between two bone surfaces. Any compression generated between surfaces is limited to the compressive forces generated by the screw threads themselves. Further, there is currently no way to effectively prevent a bone screw from loosening over time. When a screw is over-tightened and threads are stripped within the bone, or when threads strip over time as a result of micromotion, the compressive force between the facet joint surfaces will be lost and loosening will likely occur.

To prevent loosening, still other bone screws are designed such that a portion of the screw expands within the bone after the device is implanted. However, the hoop stress generated by expansion of the device within a bone makes this device ill-suited for use in the relatively small bones of the facet joint.

In attempt to create compression and prevent loosening, nut-and-bolt type assemblies have been offered as another method for immobilization of the facet joint. Using this type of assembly, a screw or "bolt" is passed through the facet joint and a nut with mating threads is placed around the screw on the back side of the facet. This approach is successful in creating compression and likely at maintaining the compression over time. However, because the nut must be introduced to the back side of the facet joint, this approach mandates a procedure that is significantly more invasive than is otherwise required.

Finally, many devices currently available for fixation of the facet joint do not contain a central hollow and therefore are not equipped for use with a guide wire, as is known in the art of orthopedic devices. Without a guide wire, placement of the device within the bones is less efficient and accuracy is more difficult. Further, small devices, such as bone screws, can be dropped and even lost within the soft tissue surrounding the site of insertion.

Because of the shortcomings associated with the currently available facet immobilization devices, physicians have largely been hesitant to attempt immobilization of the facet joint, despite the significant biomechanical and surgical benefits of doing so.

As such, there is a considerable need for a facet fixation device that can be easily and effectively inserted through a small incision and extend through the inferior and superior articular processes in order to create active compression across the facet joint and limit loosening over time.

SUMMARY

Described below is a cannulated and partially threaded bone screw assembly for the fixation of a spinal facet joint. The assembly is inserted through a very small incision near the facet joint, and has a feature that provides for the expansion of the portion of the device protruding through the superior facet of the inferior vertebrae. The expansion feature, along with the partially threaded screw shaft, serve to increase compression between the facet joint surfaces and also prevent loosening of the device over time.

In one preferred embodiment the device comprises three parts which can move with respect to one another. The three parts are an outer screw shank, an inner screw shank, and a tip. The inner shank is disposed within the outer shank. The external surface of the outer shank is partially threaded at the distal end. The external surface of the inner shank is partially threaded at the distal end, such that the distal end of the inner shank secures the tip to the screw assembly. The external surface of the tip is fully threaded. Additionally, the internal surface of the tip is threaded at the proximal end such that the inner shank can screw into the tip. Once the outer shank is positioned such that it extends through the bones, the outer shank is held stationary and the inner shank is turned. The tip is drawn into the outer shank via the threads on the inner shank which causes the outer shank to deform. The deformation caused by the tip serves to increase the size of the outer shank such that it becomes larger in diameter than the hole through which it was inserted. The deformation increases the compressive force across the facet joints and also prevents the screw from loosening or backing out of the hole through which it was inserted.

In another preferred embodiment the inner screw shank and the tip are a unitary piece. Similarly, the inner shank and the tip are disposed within the outer shank. The external surface of the outer shank is partially threaded at the distal end. Additionally, the internal surface of the outer shank is partially threaded at the proximal end. The external surface of the inner shank is partially threaded at the proximal end. The external surface of the tip is fully threaded. Once the assembly is appropriately positioned through the bones, the outer shank is held stationary and the inner shank is turned with respect to the outer shank. Due to the mating of the threads on the internal surface of the outer shank and the external surface of the inner shank, the inner shank and the tip are drawn up into the outer shank, causing the distal end of the outer shank to deform.

It should be appreciated that the above description is not meant to limit the shape of any interface surface and is presented by way of example only. For example, a hex-shaped surface of the screw and insertion tool could be modified to a Torx shape, square shape, or any other shape that provides an interference fit adequate to rotate the screw or a portion of the screw assembly. Similarly, threads may vary in length or be uniform or non-uniform in pitch, and are not limited by their depiction in the drawings.

The following Detailed Description of the invention is merely exemplary in nature and is not intended to limit the invention or the application and uses of the invention. Furthermore, there is no intention to be bound by any theory presented in the preceding Background or Summary of the Invention or the following Detailed Description of the invention. Reference will now be made in detail to exemplary embodiments of the invention, examples of which are illustrated in the accompanying drawings. The same reference numbers are used throughout the drawings to refer to the same or like parts.

DETAILED DESCRIPTION

Referring generally to FIGS. 1, 2, 3, 4 and 11, there is illustrated a first embodiment of a cannulated screw assembly 30. The cannulated screw assembly 30 is composed of an outer shank 40, an inner shank 50, and a tip 60. The tip 60 and a distal portion of the shaft 41 are threaded to such that the device may be inserted into and through two bones. It should be generally understood that while in the following description of a preferred embodiment the screw assembly 30 is described as inserted through two bones, the device may alternatively be inserted into and through two fragments of the same bone or an implantable device and a bone.

Figure 5:
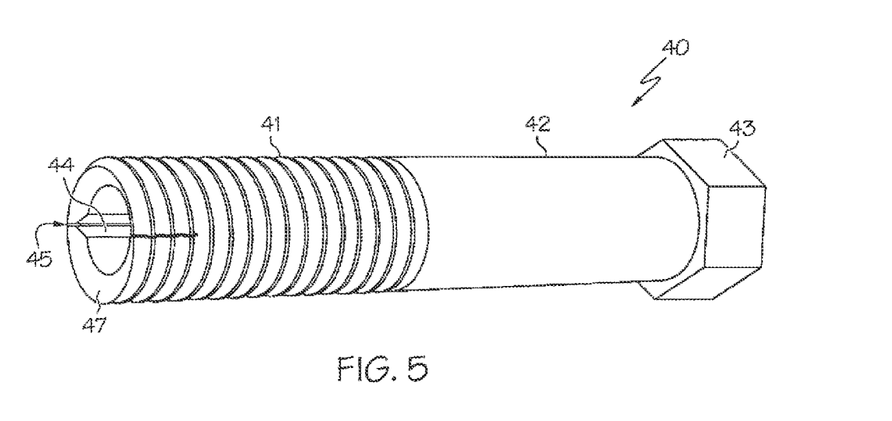
FIG. 5 is a perspective view from the distal end of the outer shank, according to the first embodiment of the invention.
Figure 6:
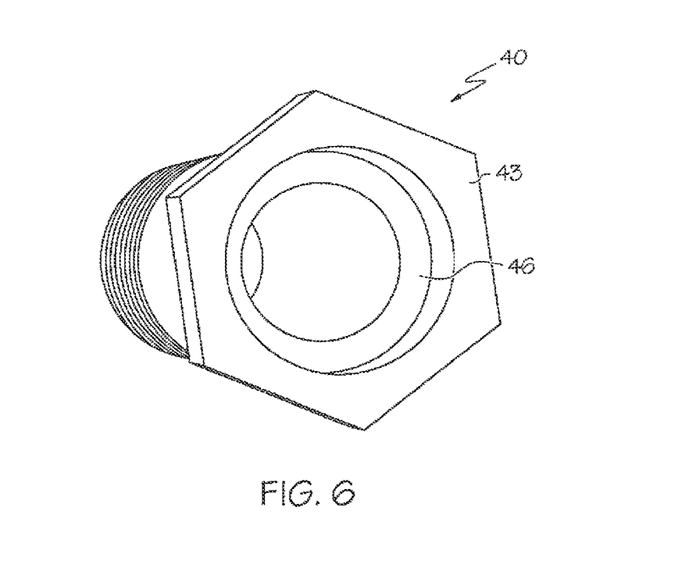
FIG. 6 is a perspective view from the proximal end of the outer shank, according to the first embodiment of the present invention.
Figure 7:
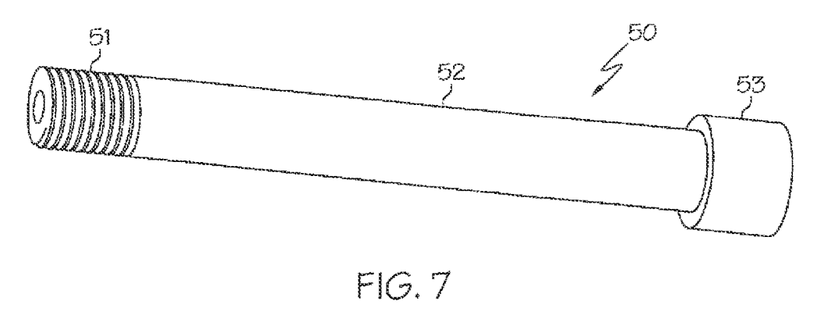
FIG. 7 is a perspective view of the inner shank, according to the first embodiment of the present invention.

As shown in FIG. 5, the outer shank 40 comprises a head 43, an unthreaded portion 42 proximal to the head 43, and the threaded portion 41 at the distal end of the outer shank 40. The outer shank 40 further includes one or more slits 45 such that the tip 60 can move into the distal end of the outer shank 40 and cause outward deformation at the distal end. The outer shank 40 further includes one or more notches 44 (shown in FIG. 5) for interaction with one or more projections 61 of the tip 60 (best seen in FIG. 8) such that the tip 60 cannot rotate with respect to the outer shank 40. Additionally, the outer shank 40 defines a chamfered edge 47, as shown in FIG. 5 and discussed below. As shown in FIG. 7, the outer shank 40 is hollow such that the inner shank 50 can be disposed within the outer shank 40.

When the screw assembly 30 is fully situated into and through two bones, the unthreaded portion 42 of the screw assembly 30 is disposed within the first bone (the bone most proximal to head 43). The threaded portion 41 is disposed within and threaded into the second bone. This arrangement provides for active compression between the bone surfaces. The length of the screw assembly 30 and the relative length of the threaded portion of the shank 41 may vary according to the variations in the anatomy of patients.

Referring now to FIG. 7, the inner shank 50 comprises a head 53, a threaded portion 51 at the distal end of the inner shank 50, and an unthreaded portion 52 proximate to the head 53. The inner shank 50 defines an interior cannulated portion 54 through which a guide wire may pass during placement of the assembly 30 within one or more bones.

Figure 1:
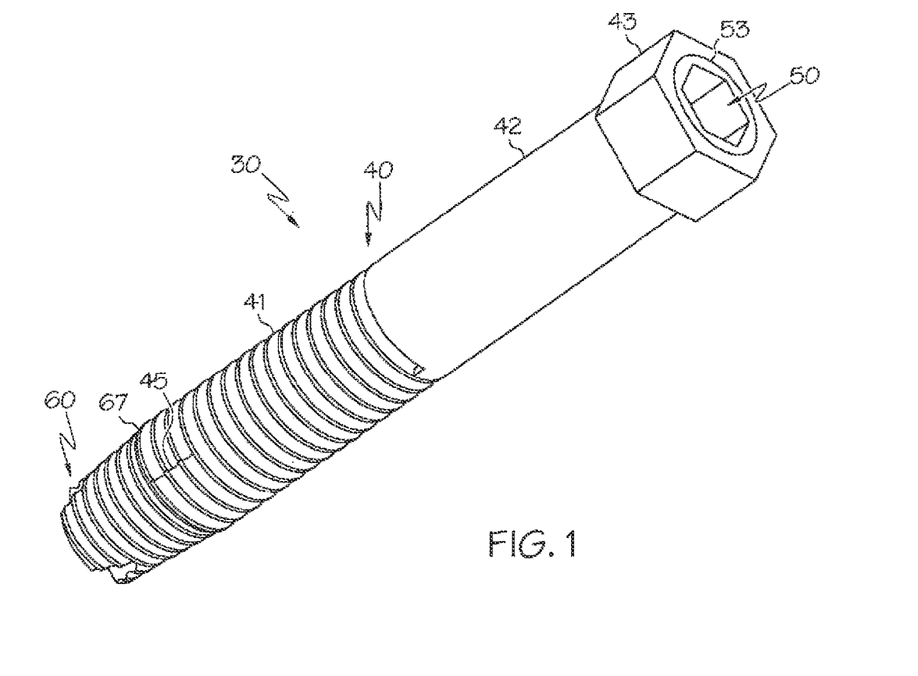
FIG. 1 is a perspective view of the cannulated screw assembly, according to the first embodiment of the invention.
Figure 2:
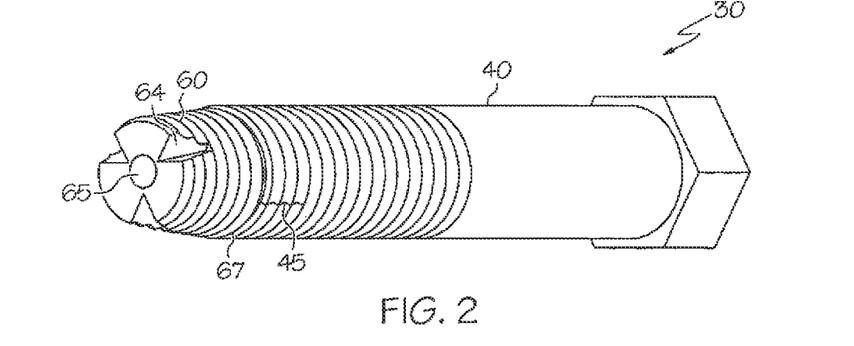
FIG. 2 is a perspective view of the distal end of the cannulated screw assembly, according to the first embodiment of the present invention.
Figure 3:
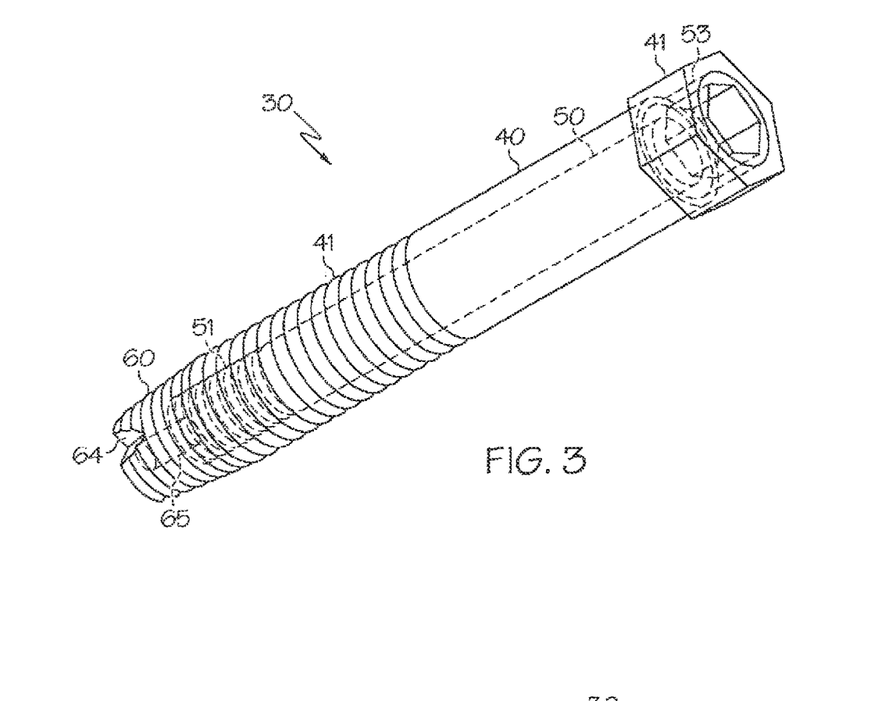
FIG. 3 is a perspective view of the cannulated screw assembly, according to the first embodiment of the present invention, wherein the outer shank and tip are shown in solid lines and the inner shank is shown using hidden lines.
Figure 4:
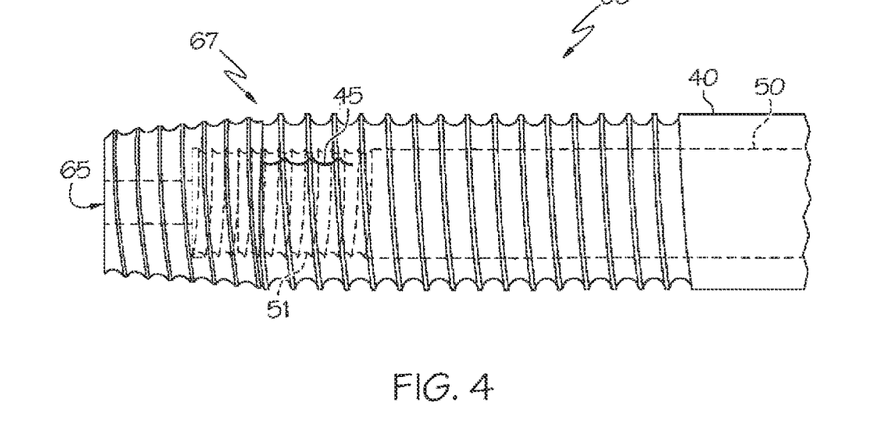
FIG. 4 is a fragmentary side view of the distal end of the cannulated screw assembly, according to the first embodiment of the invention, wherein the outer shank and tip are shown in solid lines and the inner shank is shown using hidden lines.
Figure 8:
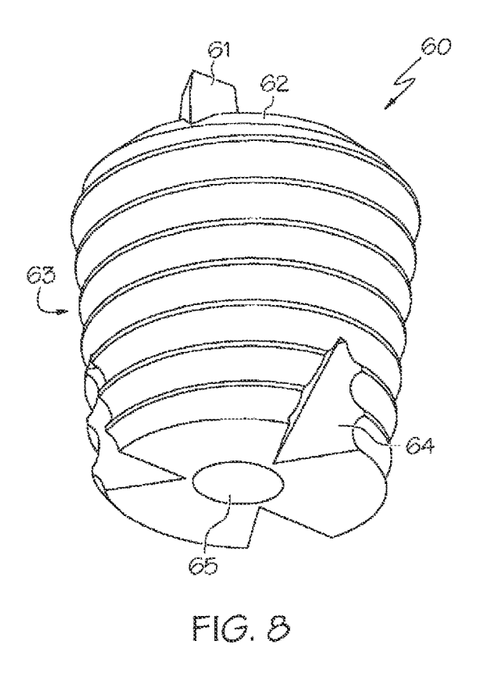
FIG. 8 is a perspective view of the tip, according to the first embodiment of the present invention.

As shown in FIG. 8, the tip 60 of the cannulated screw assembly 30 is fully threaded 63. The tip 60 also includes a chamfered edge 62, and a self-drilling groove 64. The tip 60 includes the one or more projections 61 for interaction with the one or more notches 44, such that the tip 60 does not rotate with respect to the outer shank 40. The chamfered edge 62 of tip 60 meets the mutually chamfered edge 47 of the outer shank 40 where they come together at seam 67 (FIG. 4). The tip 60 further defines a cannulated center 65 for passage of a guide wire during implantation of the device. In a preferred embodiment, the tip 60 is self-drilling and self-tapping, as known in the art.

Figure 9:
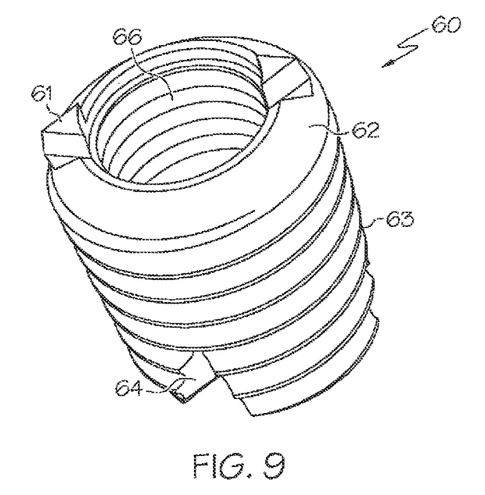
FIG. 9 is a further perspective view of the tip, according to the first embodiment of the present invention.

According to the first embodiment of the invention, and as shown in FIG. 9, the tip 60 of the cannulated screw assembly 30 also contains internal threads 66 at its proximal end to receive the threaded portion 51 at the distal end of the inner shank 50. When the inner shank 50 is rotated with respect to the outer shank 40 the mating of threads of 51 and 66 create a force that will cause the tip 60 to be drawn up into the distal end of the outer shank 40. To facilitate the movement of the tip 60 into the distal end of the outer shank 40, mutually chamfered edges, 62 and 47, create a wedge force at the seam 67 as the tip 60 is drawn up by the mating of the threads 51 and 66. Additionally, the interaction of one or more projections 61 and one or more notches 44 prevents the tip 60 from rotating with respect to the outer shank 40, thus ensuring that the force between mating threads 51 and 66 serves to move the tip 60 into the outer shank 40.

According to another embodiment, as shown in FIG. 4, a seating surface 46 within the head 43 of the outer shank 40 prevents the head 53 of the inner shank 50 from migrating into the outer shank 40 when a compressive force is created by turning the inner shank 50 as to move the tip 60 into the outer shank 40. Once the tip 60 begins to move into the outer shank 40 the distal end of the outer shank 40 will deform and become larger in diameter. To facilitate this enlargement, one or more slits 45 are created on the outer shank 40.

Figure 10:
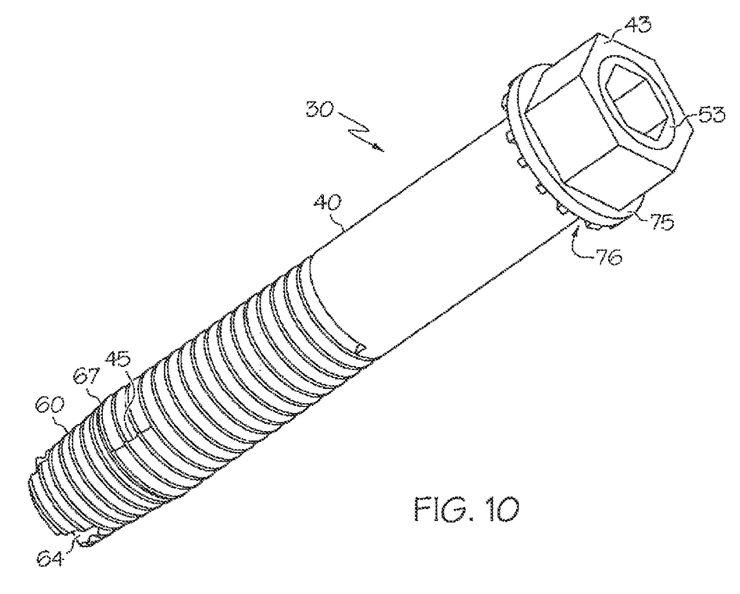
FIG. 10 is a perspective view of the cannulated screw assembly, according to a different arrangement of the present invention.
Figure 11:
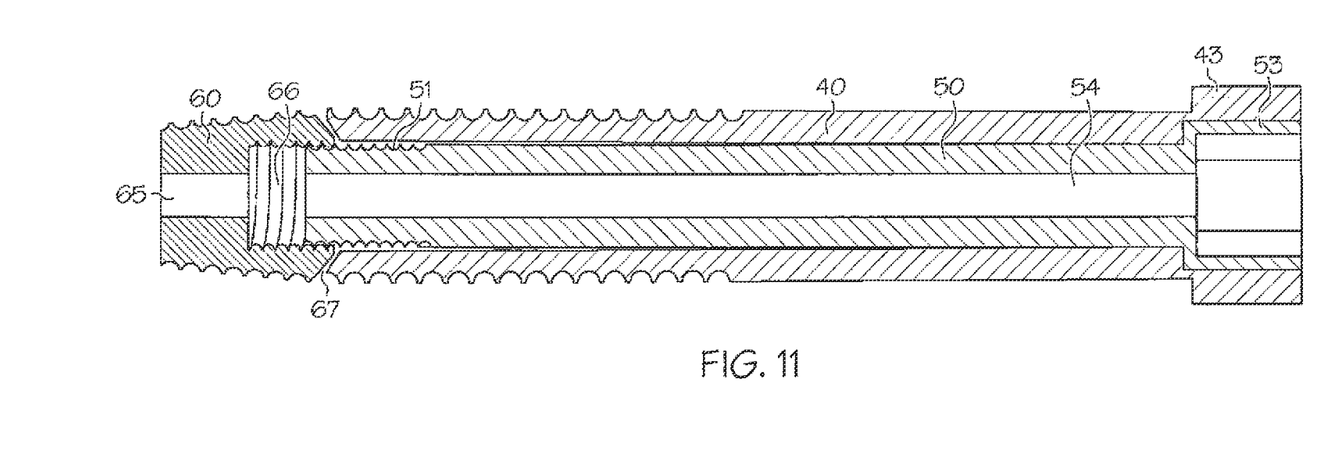
FIG. 11 is a cross-sectional view of the cannulated screw assembly, according to the first embodiment of the invention.
Figure 12:
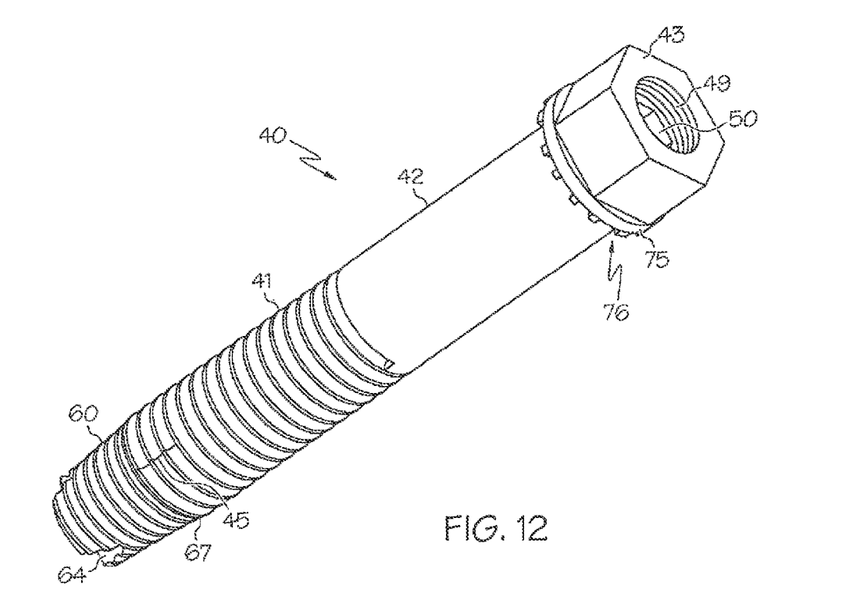
FIG. 12 is a perspective view of a cannulated screw assembly, according to a second embodiment of the present invention.

Referring next to FIG. 10 there is illustrated a further embodiment of the cannulated screw assembly 30. In this embodiment, the head portion 43 of the screw assembly 30 includes a collar 75. The collar 75 further defines a securing surface 76. The securing surface 76 may consist of any surface texture, such as smooth, rough, or ridged (as shown in FIG. 10), selected to obtain the desired amount of friction. The collar 75 is desirable in certain applications in that it provides the surface 76 which can be brought into contact with an external bone surface (not shown), in order to distribute forces and loads across the bone. Collars 75 of varying dimension can be used. In addition, if desired, an ancillary structure such as a washer (not shown) can also be interposed between the collar 75 and the bone. A washer can additionally distribute loads across a wider surface of the bone.

Figure 13:
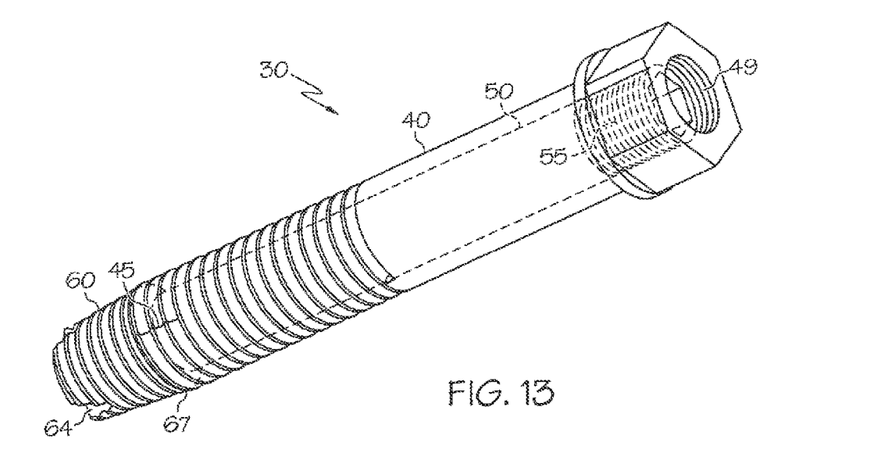
FIG. 13 is a perspective view of a cannulated screw assembly, according to the second embodiment of the present invention, wherein the outer shank and the tip are shown using solid lines and the inner shank is shown using broken lines.
Figure 14:
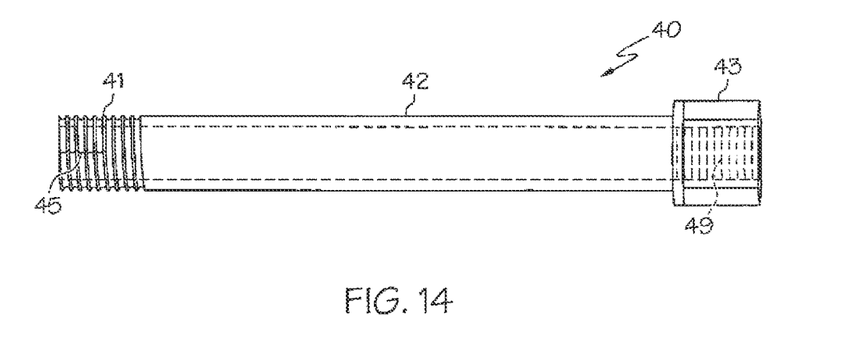
FIG. 14 is a side view of the outer shank, according to the second embodiment of the present invention.
Figure 15:
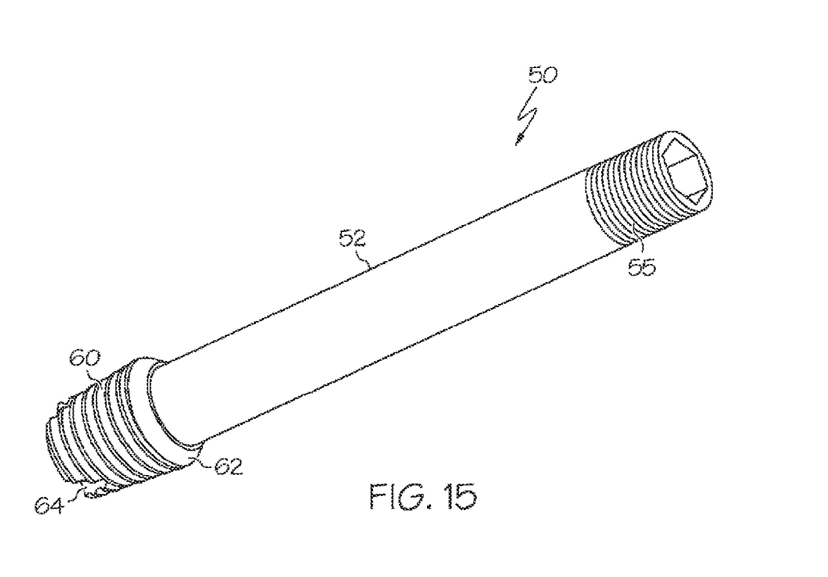
FIG. 15 is a perspective view of the inner shank and the tip, according to the second embodiment of the present invention.

According to a second embodiment of the present invention, as shown in FIGS. 12 through 16, the inner shank 50 and the tip 60 are one unitary piece. The head 43 at the proximal end of the outer shank 40 comprises an internal threading 49. As discussed with respect to the first embodiment, the shaft of the outer shank 40 further comprises the threaded portion 41, and the unthreaded portion 42. Still according to the second embodiment, and as shown in FIGS. 13 and 15, the inner shank 50 includes the unthreaded portion 52, the tip 60, and an additional external threaded portion 55 located on the external surface of the proximal end of the inner shank 50. The tip 60 comprises the outer threads 63, the self-drilling groove 64, and the cannulated center 65.

Figure 16:
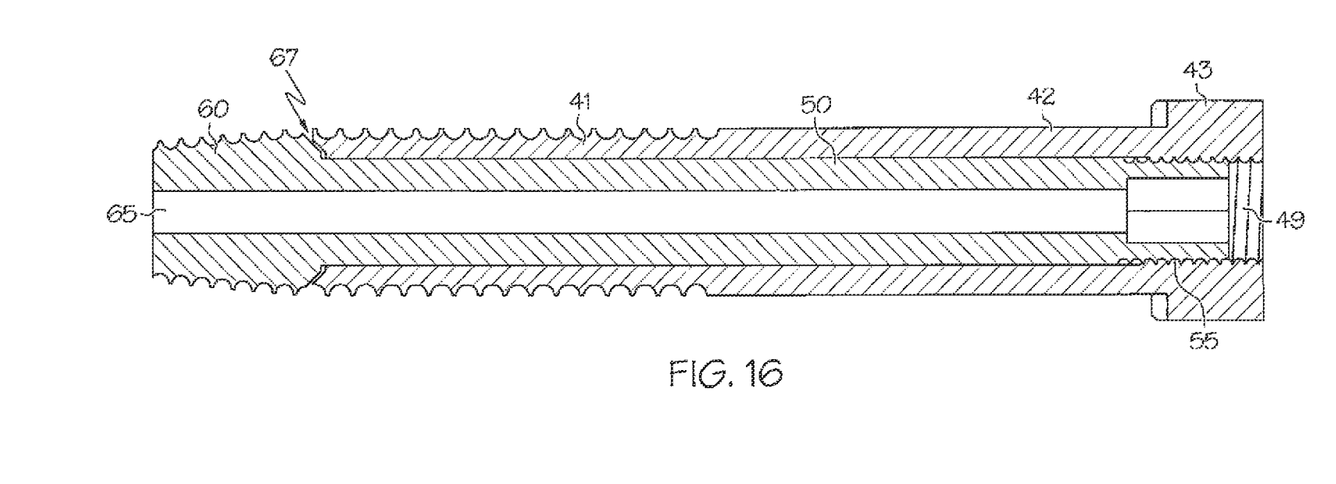
FIG. 16 is a cross-sectional view of the cannulated screw assembly, according to the second embodiment of the present invention.

According to the above described second embodiment, rotation of the inner shank 50 and tip 60 with respect to the outer shank 40 causes the internal threading 49 at the proximal end of the outer shank 40 and the external threading 55 on the proximal end of the inner shank 50 to engage as shown FIG. 16. The mating of the threads 49 and 55 creates a force that will cause the inner shank 50 and the tip 60 to be drawn up into the distal end of the outer shank 40.

The outer shank 40 of the second embodiment, like the outer shank 40 of the first embodiment, includes one or more slits 45 to facilitate deformation, and mutually chamfered tip and outer shank surfaces, 47 and 62, which meet at the interface 67 to further facilitate deformation. And similarly, the force associated with drawing the tip 60 up causes the distal end of the outer shank 40 to deform. The embodiment may further include the previously discussed collar 75 with the securing surface 76 for distributing forces and loads across the surface of a bone.

The foregoing embodiments are preferably comprised of surgical stainless steel, titanium, cobalt-chromium alloy, or any other biocompatible material as is known in the art of medical device manufacture. The cannulated screw assembly 30 may be treated with an adherent layer of hydroxyapetite, calcium phosphate, or other osteoinductive coatings as known in the art. Further, the screw assembly 30 may be treated with growth factors, stem cells, or any other device coating known in the art, to be selected based on the desired outcome of the procedure.

Figure 17:
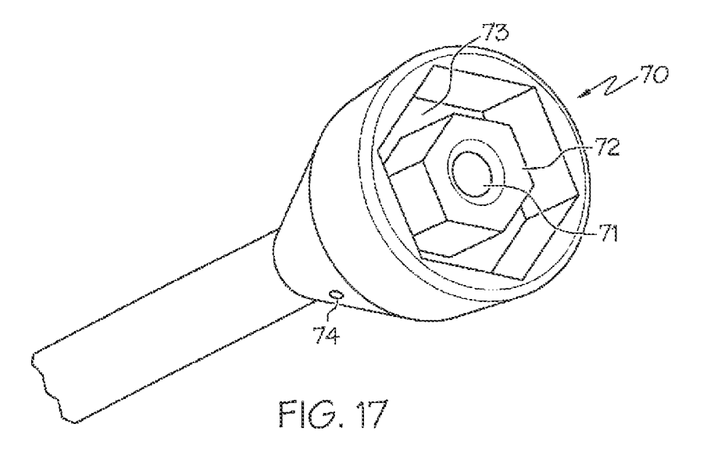
FIG. 17 is a fragmentary perspective view of a tool used to insert the cannulated screw assembly into bone.

Referring now to FIG. 17, a custom tool 70 may be used to insert the cannulated screw assembly 30 into and through the bones. The tool 70 consists of a male driver device 72, which serves as a provision for engaging and mating with the inner shank, situated within a female driver device 73, which serves as a provision for engaging and mating with the outer shank. In this case they are portrayed as a male and female hexagonal-shaped driver, but other shapes are viable options. The tool 70 is cannulated 71 to allow a guide wire, such as a KIRSCHNER or "K" wire, to pass through. The tool 70 will initially ensure that the inner and outer screw shanks, 40 and 50, rotate at the same rate when inserting the screw assembly 30 into and through the bones. This will prevent premature and undesired rotation of the inner shank 50 with respect to the outer shank 40 as the outer shank 40 is placed into bone. Turning the inner shank 50 prior to final placement is undesirable because it will cause expansion of the outer shank 40. Once the screw assembly 30 is in the desired orientation, the tool 70 having the male driver device 72 can be used to rotate the inner shank 50 with respect to the outer shank 40 and thereby cause the desired deformation of the outer shank 40.

The male driver device 72 and the female driver device 73 are preferably comprised within a single tool 70 including an additional locking mechanism (shown as a simple set screw 74) such that the user has the capacity to lock and unlock the ability of the male driver portion 72 to rotate with respect to the outer female driver portion 73. The above described tool is desirable because (i) it ensures that while the outer shank 40 is being deformed by the motion of the inner shank 50 and tip 60, the outer shank 40 does not turn within the bone, and (ii) it eliminates the added step of changing tools during insertion of the screw assembly 30. Other equivalent locking and unlocking mechanisms for this purpose will be apparent to those skilled in the art. For example, the male driver portion 72 and the female driver portion 73 may be mounted on coaxial cannulated stems relatively axially moveable to a small degree to engage teeth or other interengageable blocking parts interfitting between portions 72 and 73 to prohibit and permit relative rotation with respect to each other. Less desirable, but still within the inventive concept, two different tools may be used—one in which the portions 72 and 73 are fixed with respect to each other for placing the screw assembly 30, and one in which the portions 72 and 73 are rotatable with respect to each other to allow the inner shank to be rotated with respect to the outer shank in order to expand the tip, once the screw assembly is in place. In another alternative and less desirable embodiment, the male driver portion 72 and the female driver portion 73 may be two separate tools.

The cannulated screw assembly 30 can be inserted into and through two bones as follows. First, a guide wire, such as a small diameter "K" wire, is inserted into and through the two bones, generally using fluoroscopic imaging, as is known in the art. Second, the cannulated screw assembly 30 is placed over the guide wire. Alternatively, the guide wire may be placed through the screw assembly 30 before the wire is threaded into and through the bones. With the custom tool 70, using the self-drilling and self-tapping capacity if necessary, the screw assembly 30 is inserted into and through the bones until the distal tip 60 of the screw assembly 30 is protruding through the second bone. Finally, the inner shaft 50 is rotated with respect to the outer shank 40 using the custom tool 70, such that the tip 60 is moved up into the outer shank 40 causing deformation of the distal end of the outer shank 40. The deformation of the outer shank 40 causes the distal end of the outer shank 40 to permanently expand in diameter outside of and adjacent to the external surface of the more distal bone, thus providing additional compression between the bones and limiting or preventing loosening over time.

Referring again to FIG. 18, it is noted that neighboring vertebrae come into proximity at the facet or zygapophyseal joint 84. The facet joint 84 includes a superior articular process 82 of one vertebra and an inferior articular process 83 of a second vertebra. One manner of connecting the vertebrae through the zygapophyseal joint using the cannulated screw assembly 30 is illustrated. In the illustrated embodiment, the screw assembly 30 links two proximate vertebrae. The screw assembly 30 generally extends beyond the external surface of each of the bone protrusions that are linked by the assembly 30. In the illustrated embodiment, the screw assembly 30 is positioned with the head situated in a generally medial orientation. Alternatively, a screw assembly can be positioned with a generally lateral configuration. In other embodiments, the screw assembly 30 can have a different position and need not protrude from the bone to the extent illustrated. It is also to be appreciated that other sections of the same two vertebrae can also be joined. For example, the second facet joint 84, which is positioned opposite the first facet joint 84 may be joined by a second screw assembly 30. In many circumstances it may be preferable to use the cannulated screw assembly 30 in connection with an interbody device (not shown) in order to achieve maximum immobilization of the spinal section.

The above described embodiments provide significant advantages over the devices found in the prior art. Specifically, the deformation of the distal end of the outer shank 40 outside and adjacent to the external surface of the bone provides enhanced compression of the bones and prevents the screw assembly 30 from loosening within the bone, preventing discomfort and damage to the joint or surrounding tissues. The partially threaded shaft 41 of the screw assembly 30 further aides in creating compression and maintaining the compression over time. The cannula that extends throughout the center of the device allows for use of a guide wire, enabling effective and efficient placement of the device. As such, the screw assembly 30 is useful in a variety of applications, including fixation of the facet joint, orthopedic fracture fixation, and anchoring an implantable orthopedic device to bone.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out this invention, but that the invention will include all embodiments falling within the scope of the general description.

What is claimed is:

1. A method of inserting a multipart expandable screw assembly into first and second articulating bones of a facet joint of a patient, the method comprising:
   engaging a cannulated screw assembly with a placement tool, the cannulated screw assembly comprising an outer cannulated shank and an inner cannulated shank partially received within the outer shank in a first unexpanded configuration, such that a distal tip of the cannulated inner shank extends distally beyond a distal end of the cannulated outer shank prior to insertion of the cannulated screw assembly into the facet joint,
   the placement tool having a longitudinal axis and comprising:
   a stem;
   a head carried on the stem, wherein the head has a male driver and a female driver, wherein the female driver receives and rotationally engages an external surface of a proximal end of the cannulated outer shank of the cannulated screw assembly, and wherein the male driver is received within and rotationally engages an inner surface of a proximal end of the cannulated inner shank of the cannulated screw assembly; and a locking mechanism, actuating the locking mechanism to rotationally lock the male driver of the placement tool to the female driver of the placement tool about the longitudinal axis of the placement tool;

with the male driver rotationally locked to the female driver, rotating the stem of the placement tool about its longitudinal axis to rotate the male and female drivers of the placement tool together to rotate and insert the cannulated screw assembly in the first unexpanded configuration into the first articulating bone and the second articulating bone until the distal tip of the cannulated inner shank of the cannulated screw assembly protrudes through the second articulating bone of the facet joint;

with the distal tip of the cannulated inner shank of the cannulated screw assembly protruding through the second articulating bone of the facet joint, disengaging the locking mechanism from the placement tool to rotationally decouple the female driver of the placement tool from the male driver of the placement tool; and with the female driver rotationally decoupled from the male driver, preventing rotation of the outer shank of the cannulated screw assembly by holding the female driver of the placement tool in a stationary rotational position, such that the proximal and distal ends of the cannulated outer shank of the cannulated screw assembly are prevented from rotation in the first and second articulating bones of the facet joint, while rotating the cannulated inner shank of the cannulated screw assembly by rotating the male driver of the placement tool, such that the proximal end and the distal tip of the cannulated inner shank of the cannulated screw assembly are rotated relative to the cannulated outer shank of the cannulated screw assembly to draw the distal tip of the cannulated inner shank of the cannulated screw assembly proximally into the cannulated outer shank and cause deformation and radial expansion of the distal end of the outer shank adjacent to an external surface of the second articulating bone element in a second expanded configuration, while the proximal end of the cannulated outer shank of the screw assembly is secured to the first articulating bone.

2. The method of claim 1, further comprising:
prior to engaging the cannulated screw assembly with the placement tool, inserting a guide wire through the first and the second articulating bones; and
placing the cannulated screw assembly over the guide wire.

3. The method of claim 1, wherein the male driver of the head of the placement tool comprises a male hexagonal-shaped driver, and wherein the female driver of the head of the placement tool comprises a female hexagonal-shaped driver.

4. The method of claim 1, wherein the locking mechanism comprises a set screw.

5. The method of claim 1, wherein, with the male driver of the placement tool rotationally locked to the female driver of the placement tool, rotating the male and female drivers of the placement tool comprises rotating the male and female drivers of the placement tool at the same rate.

6. The method of claim 2, wherein the stem of the placement tool is cannulated, and wherein engaging the cannulated screw assembly with the placement tool comprises passing the guide wire through the stem of the placement tool and through the cannulated screw assembly to guide the screw assembly to a desired situs.

7. The method of claim 1, wherein the male driver is situated within the female driver.

8. The method of claim 1, wherein the distal tip of the inner shank of the cannulated screw assembly has a threaded outer surface.

9. The method of claim 8, wherein the distal end of the outer shank has a threaded outer surface.

10. The method of claim 9, wherein the threaded outer surfaces of the distal tip of the inner shank and the distal end of the outer shank cooperate to define a threaded outer surface of the cannulated screw assembly during insertion of the cannulated screw assembly into the first and second articulating bones.

* * * * *